United States Patent
Scurtescu et al.

(10) Patent No.: US 10,495,523 B2
(45) Date of Patent: Dec. 3, 2019

(54) APPARATUSES AND METHODS FOR MEASURING AND CHARACTERIZING ULTRASOUND

(71) Applicant: SMILESONICA INC., Edmonton (CA)

(72) Inventors: Cristian Scurtescu, Edmonton (CA); Ilya Utkin, Edmonton (CA)

(73) Assignee: SMILESONICA INC., Edmonton (CA)

( * ) Notice: Subject to any disclaimer, the term of this patent is extended or adjusted under 35 U.S.C. 154(b) by 309 days.

(21) Appl. No.: 15/110,379

(22) PCT Filed: Jan. 7, 2015

(86) PCT No.: PCT/CA2015/000004
§ 371 (c)(1),
(2) Date: Jul. 7, 2016

(87) PCT Pub. No.: WO2015/103690
PCT Pub. Date: Jul. 16, 2015

(65) Prior Publication Data
US 2016/0334283 A1 Nov. 17, 2016

Related U.S. Application Data

(60) Provisional application No. 61/925,219, filed on Jan. 8, 2014.

(51) Int. Cl.
*G01K 11/22* (2006.01)
*G01H 3/10* (2006.01)
(Continued)

(52) U.S. Cl.
CPC .............. *G01K 11/22* (2013.01); *G01H 3/10* (2013.01); *G01K 17/00* (2013.01); *A61C 7/00* (2013.01); *G10K 11/02* (2013.01)

(58) Field of Classification Search
CPC .......... G01K 11/22; G01K 17/00; G01H 3/10; G10K 11/02; A61C 7/00
(Continued)

(56) References Cited

U.S. PATENT DOCUMENTS 6,490,470 B1 12/2002 Kruger
6,978,677 B2 12/2005 Bajram
(Continued)

FOREIGN PATENT DOCUMENTS

EP 0089841 A1 9/1983
WO 2011134071 A1 11/2011

OTHER PUBLICATIONS

Fay B. et al., "The Thermoacoustic effect and its use in ultrasonic power determination", Ultrasonics, IPC Science and Technology Press Ltd. Guildford, GB, vol. 34, No. 2, Jun. 1, 1996 (Jun. 1, 1996), pp. 563-566, XP004035692, ISSN: 0041-624X, DOI: 10.1016/0041-624X(96)00044-3 Jun. 1996.
(Continued)

*Primary Examiner* — Yartiza Guadalupe-McCall
(74) *Attorney, Agent, or Firm* — Marsh Fischmann & Breyfogle LLP; Jonathon A. Szumny; Thomas R. Marsh

(57) ABSTRACT

Apparatuses and methods for measuring and characterizing ultrasound using thermoacoustic sensors are provided. Thermoacoustic sensors can include heat flux sensors for detecting a temperature difference (between the front and back of the heat flux sensor) and an absorber layer attached to the heat flux sensor for absorbing ultrasound, converting it to heat, and also acting as an acoustic impedance matching layer. An heat sink can also be used. In some embodiments, thermoacoustic sensors can be arranged into an acoustic integrating sphere and face inward to form a cavity. The sphere can have an opening to the cavity, wherein ultrasound emitted through the opening can cause a temperature dif-
(Continued)

ference that can be detected by the thermoacoustic sensors. These apparatuses and others can provide for methods of measuring ultrasound power and/or methods of determining an ultrasound profile as the angular distribution of emitted ultrasound power generated by an ultrasound transducer.

13 Claims, 15 Drawing Sheets

(51) Int. Cl.
  *G01K 17/00*   (2006.01)
  *A61C 7/00*   (2006.01)
  *G10K 11/02*   (2006.01)

(58) Field of Classification Search
  USPC .......................................................... 374/29
  See application file for complete search history.

(56) References Cited

U.S. PATENT DOCUMENTS

| | | | |
|---|---|---|---|
| 6,994,468 B2 | 2/2006 | Thery et al. | |
| 7,318,671 B1* | 1/2008 | Moghaddam | G01N 25/18 374/30 |
| 8,256,953 B2 | 9/2012 | Yuhas et al. | |
| 2005/0016282 A1 | 1/2005 | Bajram | |
| 2012/0010510 A1* | 1/2012 | Zeqiri | A61B 8/00 600/459 |
| 2012/0123256 A1 | 5/2012 | Razansky et al. | |
| 2012/0320710 A1 | 12/2012 | Sato et al. | |
| 2013/0265856 A1 | 10/2013 | Choi et al. | |
| 2015/0204733 A1* | 7/2015 | Newell | G01K 1/14 374/141 |
| 2016/0178583 A1* | 6/2016 | Ntziachristos | A61B 5/0095 73/643 |
| 2016/0178680 A1* | 6/2016 | Ntziachristos | A61B 5/0095 73/643 |
| 2016/0334283 A1* | 11/2016 | Scurtescu | G01K 11/22 |

OTHER PUBLICATIONS

Bajram Zeqiri et al., "A Novel Pyroelectric Method of Determining Ultrasonic Transducer Output Power: Device Concept, Modeling, and Preliminary Studies", IEEE Transactions on Ultrasonics, Ferroelectrics and Frequency Control, IEEE, US, vol. 54, No. 11, Nov. 1, 2007 (Nov. 1, 2007), pp. 2318-2330, XP011198613, ISSN: 0885-3101, DOI: 10.1109/TUFFC.2007.536 Nov. 1, 2007.
Fay B. et al., "Thermoacoustic sensor for ultrasound power measurements and ultrasonic equipment calibration", Ultrasound in Medicine and Biology, New York, NY, US, vol. 20, No. 4, Jan. 1, 1994 (Jan. 1, 1994), pp. 367-373, XP026418327, ISSN: 0301-5629 Jan. 1, 1994.
Zeqiri B, J Barrie, Ultrasound in Med.&Biol., vol. 34, 1513 2008.
Thermo-acoustic ultrasound sensor from GAMPT mbH http://www.gampt.de/content/cms/front_content.php?idcat=257 Feb. 4, 2016.
Wilken V, Measurement Sc. & Techn., vol. 21, 115805 2010.
Wilken V, Measurement Sc. & Techn., vol. 21, 115806 2010.
Martin C.J, Law A.N.R., Ultrasonics, 127 1980.
Preston, R. C. (Ed.) Output Measurements for Medical Ultrasound 1991.
Romdhane, M., et al., Ultrasonics, vol. 33 No. 2 1995.
Fay, B, M Rinker, Ultrasonics, vol. 34 1996.
Zieniuk, J. K., Ultrasonics, 136 1966.
WElls, P.N.T., et al., Ultrasonics, 106 1963.
Torr, G. R., D.J. Watmough, Phys. Med. Biol., vol. 22 No. 3 444-450 1977.
Fry, W. J., R. B. Fry, J. Acoust. Soc. Am. 26, 311 1954.
Romdhane, M., et al., Ultrasonics, vol. 34 835 1996.
Mikhailov, I. G., Ultrasonics, 129 1964.
Campolo, D. (Ed.) New Developments in Biomedical Engineering, Gutierrez, M.I., et al. Method for Characterizatin of Physiotherapy Ultrasonic Transducers 2010.
Pullano, S.A., et al., Proceedings of the 3rd International Conference on E-Health and Bioengineering 2011.
Lubbers J., J. Schortinghuis, The weight of 15 MHz ultrasound. Calibration of a therapeutic unit for small animals. 2004.

* cited by examiner

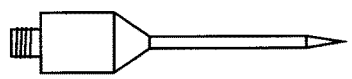
Figure 1A
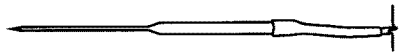
Figure 1B
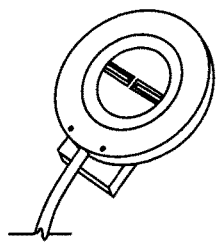
Figure 1D
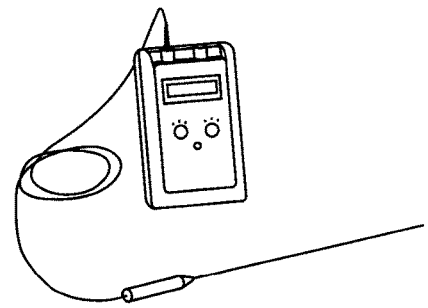
Figure 1C
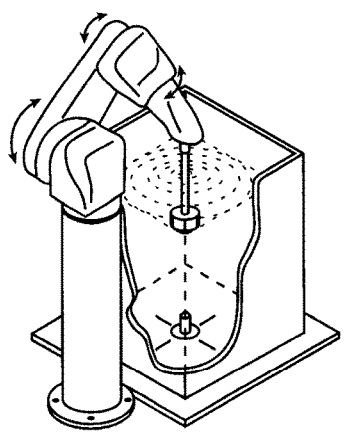
Figure 1E
Figure 1F
Figure 1 (Prior Art)

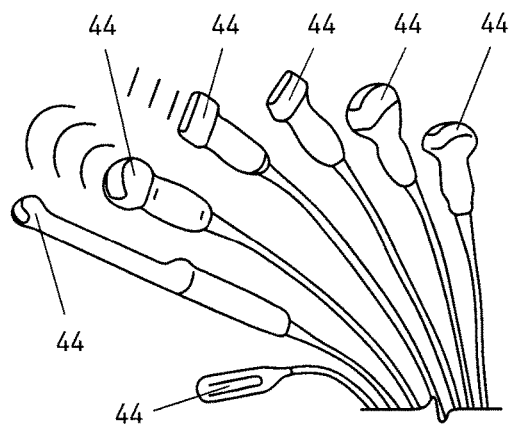
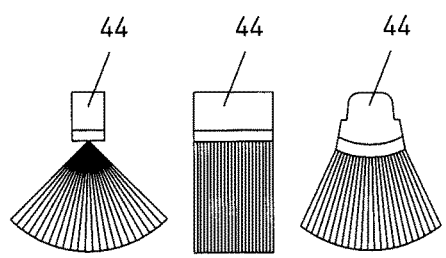
Figure 6A
Figure 6B
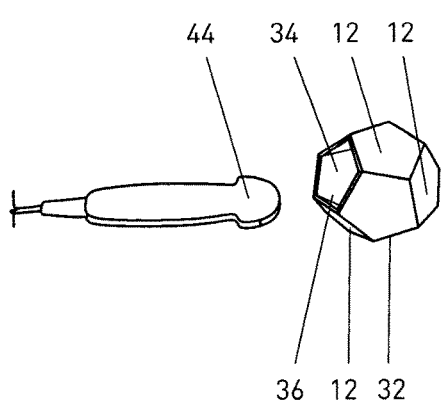
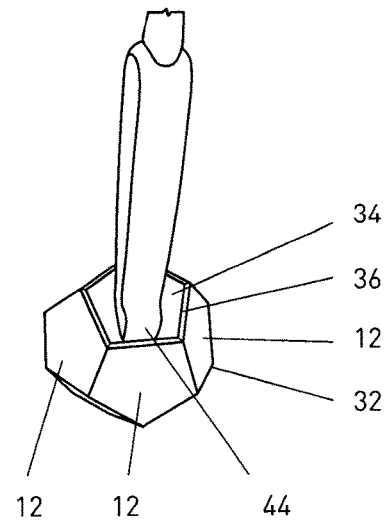
Figure 6C
Figure 6D

APPARATUSES AND METHODS FOR MEASURING AND CHARACTERIZING ULTRASOUND

RELATED APPLICATIONS

This application claims the benefit of U.S. Provisional Application No. 61/925,219, entitled "Apparatuses and Methods for Measuring and Characterizing Ultrasound", filed on Jan. 8, 2014, which is herein incorporated by reference.

TECHNICAL FIELD

The present application relates to apparatuses and methods for measuring and characterizing ultrasound, and more particularly, apparatuses and methods for measuring and characterizing ultrasound using thermoacoustic sensors.

BACKGROUND

By way of background, ultrasound transducers in medical ultrasound emitting devices can be used for purposes such as therapeutic, imaging, or interventional ultrasound. The total power emitted by the transducer head is an important parameter that needs to be measured and calibrated prior to use on patients. In addition, the power emissions should be monitored periodically during normal operation and/or when servicing/repairing the ultrasound equipment or device. These ultrasound emitting devices are also regulated by certain industry standards for therapeutic, imaging, and interventional ultrasound.

Current apparatuses and methods of measuring ultrasound power from these devices can be time consuming (involving the time and high cost of skilled technicians), bulky (with limited or only partial portability), or not sufficiently accurate. Inaccuracy is particularly a problem when the ultrasound emitting head on the device to be measured has an array of transducers (either multiple individual transducers, or multiple transducer elements on a single transducer substrate) and/or complex shape or beam profiles. In some cases, the ultrasound can have diverging or converging beams, or both diverging and converging beams but in different planes, making the ultrasound power difficult to measure.

Currently the industry approach to determine the total emitted power of an ultrasound head is to use either a scanning technique with a calibrated hydrophone, a reactive force balance technique, or a thermoacoustic technique. Please see FIG. 1 for examples of these prior art devices. These existing apparatuses and techniques have certain limitations and disadvantages.

The hydrophone technique is very time consuming as it requires an accurate measurement of the ultrasound wave pressure in multiple points. Since both the ultrasonic beam from the transducer, and the receiving response of the hydrophone are strongly directional, alignment is crucial in the measurement procedure. In order to align the hydrophone properly, a suitable mount must be used. There are two types of hydrophones: needle and membrane. Membrane hydrophones should be clamped to the mount by their supporting ring with the front of the hydrophone (the side where the ring is almost flush with the membrane) nearest the transducer. Probes/needles should be clamped several centimeters back from the sensitive element. The hydrophone mount should have five degrees of freedom. It should be possible to move the hydrophone by translation in three orthogonal directions, one of which should be parallel to the direction of propagation of the ultrasound. It should also be possible to rotate and tilt the hydrophone, ideally with the axes of rotation and tilt passing through the active element.

The radiative force balance technique can provide accurate measurements for the transducer heads that emit ultrasound wave with low divergence (plane waves/parallel beam), however it can only measure power from a single transducer sitting flat and aligned on top of the cone target.

These balance instruments use a positioning clamp to hold the transducer in de-gassed water above a conical target. The ultrasonic energy passes through the water, reflects from the target cone, and is then absorbed by the rubber lining. The radiant power is directly proportional to the total downward force on the target. This force is then transferred through the target support assembly to a digital scale that displays the power in watts of power or grams of force. These power meters however, cannot measure power from a non-planar transducer, non-planar arrays of transducers, or transducers emitting inside a cavity. There remains a need to provide apparatuses and methods for measuring and characterizing ultrasound, that can overcome the shortcomings of the prior art.

SUMMARY

Apparatuses and methods for measuring and characterizing ultrasound using thermoacoustic sensors are provided. A thermoacoustic sensor can include a heat flux sensor for detecting a temperature difference (between the front and back of the heat flux sensor) and a rubber absorber layer attached to the heat flux sensor for absorbing ultrasound, converting it to heat, and also acting as an acoustic impedance matching layer. An optional heat sink can also be used. In some embodiments, thermoacoustic sensors can be arranged into an acoustic integrating sphere and face inward to form a cavity. The sphere can have an opening to allow access to the cavity, wherein ultrasound emitted through the opening of the sphere causes a temperature difference that can be detected by the thermoacoustic sensors. These apparatuses and others can provide for methods of measuring ultrasound power and/or methods of determining an ultrasound profile as the angular distribution of emitted ultrasound power generated by an ultrasound transducer.

In some embodiments, the thermoacoustic sensors can be arranged in a non-flat array to match the shape of the head of an ultrasound emitting device.

In some embodiments, the methods and apparatuses of the present disclosure can simplify the procedure of measuring the total output power from medical and industrial ultrasound devices with transducers heads of various shapes, number of emitting elements, beam profiles or power, in a single instrument (such as an acoustic integrating sphere). In addition, some embodiments can provide an angular distribution of emitted ultrasound power.

Furthermore, an acoustic integrating sphere as presented herein can be portable (handheld), can be connected to a computer or have its own embedded computing capability, can be operated in noisy (sound wise) environments, can operate in a water bath without ultrasound absorbing walls, and can be operated on any surface/table (as it is not sensitive to vibrations). All these features can bring this instrument closer to where the ultrasound devices are used in the field, reducing the time and costs involved in calibration, and better ensuring the safety of the ultrasound emitting device.

Broadly stated, in some embodiments, a thermoacoustic sensor for measuring ultrasound is provided, the sensor comprising: a heat flux sensor for detecting a temperature difference (between the front and back of the heat flux sensor); and an ultrasound absorbing layer attached to the heat flux sensor for absorbing ultrasound and converting it to heat, the ultrasound absorbing layer also acting as an acoustic impedance matching layer.

In some embodiments, the thermoacoustic sensor can further comprise a heat sink attached to the heat flux sensor for dispersing heat. In some embodiments, the heat sink can be made of copper. In some embodiments, the ultrasound absorbing layer and heat sink are on opposite sides of the heat flux sensor. In some embodiments, the ultrasound absorbing layer can be made of a material selected from the group consisting of butyl rubber, ethylene propylene rubber, polyurethane rubber, and silicone rubber. In some embodiments, the heat flux sensor can comprise a flexible array of heat flux sensors. In some embodiments, the thermoacoustic sensor can further comprise means for reporting a temperature difference (between the front and back of the heat flux sensor) detected by the heat flux sensor, the means for reporting a temperature difference can be in electronic communication with the heat flux sensor. In some embodiments, means for reporting a temperature difference can comprise software configured for converting the temperature difference to data. In some embodiments, the software can be further configured for converting the data to a measurement of ultrasound power.

Broadly stated, in some embodiments, an acoustic integrating sphere is provided, the sphere comprising: multiple thermoacoustic sensors arranged into a sphere like shape and facing inward to form a cavity; and an opening formed by the sensors to allow access to the cavity; wherein ultrasound emitted through the opening of the sphere causes a temperature difference that is detected by the thermoacoustic sensors.

In some embodiments, the thermoacoustic sensors of the sphere can be the thermoacoustic sensor as described herein. In some embodiments, the sensors can be shaped to form facets of the sphere. In some embodiments, the sensors can be pentagon shaped. In some embodiments, the sphere can be configured to be filled with liquid to maintain a constant temperature in the absence of being exposed to ultrasound and to distribute heat in the presence of ultrasound. In some embodiments, the sphere can further comprise means for reporting a temperature difference detected by the thermoacoustic sensor, the means for reporting a temperature difference can be in electronic communication with the thermoacoustic sensor. In some embodiments, the means for reporting a temperature difference comprises software that can be configured for converting the temperature difference to data. In some embodiments, the software can further be configured for converting the data to a measurement of ultrasound power and/or an ultrasound profile (power spatial distribution).

Broadly stated, in some embodiments, a method of measuring ultrasound power is provided, the method comprising: providing an ultrasound measuring apparatus, the apparatus comprising a thermoacoustic sensor for measuring ultrasound; positioning the transducer proximate the measuring apparatus; emitting ultrasound from the transducer; exposing the measuring apparatus to the ultrasound emitted from the transducer; converting the ultrasound to data; and creating a measurement of ultrasound from the data.

In some embodiments, the measuring apparatus can be a thermoacoustic sensor as described herein. In some embodiments, the measuring apparatus can be an acoustic integrating sphere as described herein. In some embodiments, the step of converting the ultrasound to data further comprises converting the ultrasound to heat to create a temperature difference and converting the temperature difference to data.

Broadly stated, in some embodiments, a method is provided for determining an ultrasound profile as the angular distribution of emitted ultrasound power generated from an ultrasound transducer, the method comprising: providing an ultrasound measuring apparatus, the apparatus comprising a thermoacoustic sensor for measuring ultrasound; positioning the transducer proximate the measuring apparatus; emitting ultrasound from the transducer; exposing the measuring apparatus to the ultrasound emitted from the transducer; converting the ultrasound to data; and creating an ultrasound profile from the data.

In some embodiments, the measuring apparatus can be an acoustic integrating sphere as described herein. In some embodiments, the step of converting the ultrasound to data further comprises converting the ultrasound to heat to create a temperature difference and converting the temperature difference to data.

BRIEF DESCRIPTION OF THE DRAWINGS

FIG. 1 depicts various embodiments of prior art devices for measuring ultrasound power. FIGS. 1A and 1B depict ultrasound needle hydrophones, FIG. 1C depicts an ultrasound needle hydrophone connected to its electronic controller, FIG. 1D depicts an ultrasound membrane hydrophone, FIG. 1E depicts an ultrasound hydrophone scanning setup, and FIG. 1F depicts a reactive force balance ultrasound power meter.

FIG. 6A is a front perspective view depicting prior art embodiments of ultrasound emitting devices.

FIG. 6B is a schematic diagram of a top view depicting embodiments of beam profiles.

FIG. 6C is a side perspective view depicting an embodiment of an acoustic integrating sphere and an ultrasound emitting device, the sphere positioned in a non-measuring position.

FIG. 6D is a top perspective view depicting the acoustic integrating sphere and an ultrasound emitting device of FIG. 6C, the sphere positioned in a measuring position.

DETAILED DESCRIPTION OF EMBODIMENTS

Apparatuses and methods for measuring and characterizing ultrasound using thermoacoustic sensors are provided. A thermoacoustic sensor can include a heat flux sensor for detecting a temperature difference (between the front and back of the heat flux sensor) and a rubber absorber layer attached to the heat flux sensor for absorbing ultrasound, converting it to heat, and also acting as an acoustic impedance matching layer. An optional heat sink can also be used. In some embodiments, thermoacoustic sensors can be arranged into an acoustic integrating sphere and face inward to form a cavity. The sphere can have an opening to allow access to the cavity, wherein ultrasound emitted through the opening of the sphere causes a temperature difference that can be detected by the thermoacoustic sensors. These apparatuses and others can provide for methods of measuring ultrasound power and/or methods of determining an ultrasound profile as the angular distribution of emitted ultrasound power generated by an ultrasound transducer.

The apparatuses and methods as described herein are based on the thermal effect of an acoustic wave where an incident ultrasound wave is absorbed by an ultrasound absorbing material able to convert it into heat.

Figure 2A:
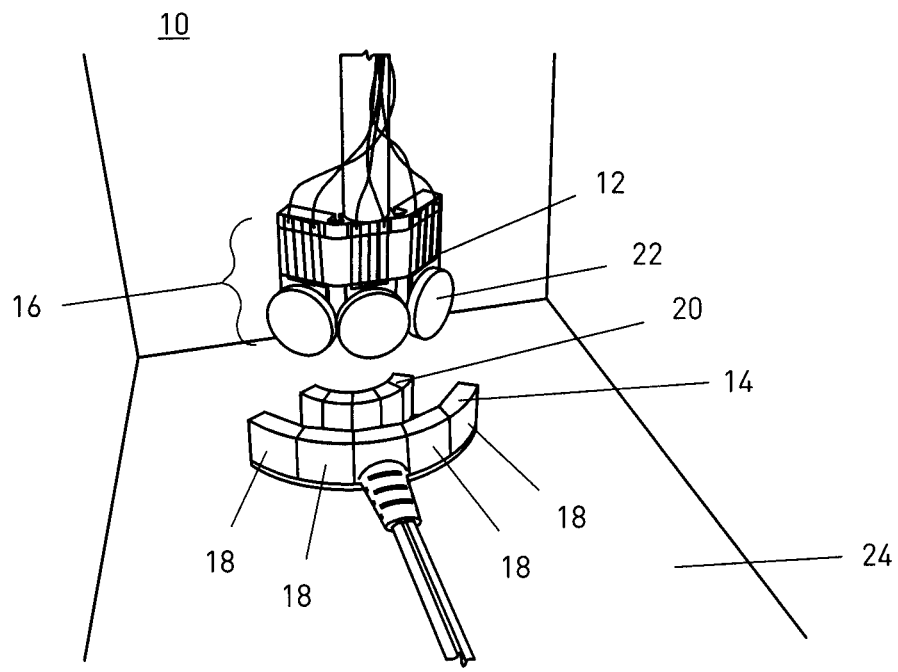
FIG. 2A is a front perspective view depicting an embodiment of an apparatus for measuring ultrasound power, the apparatus positioned in a non-measuring position.
Figure 2B:
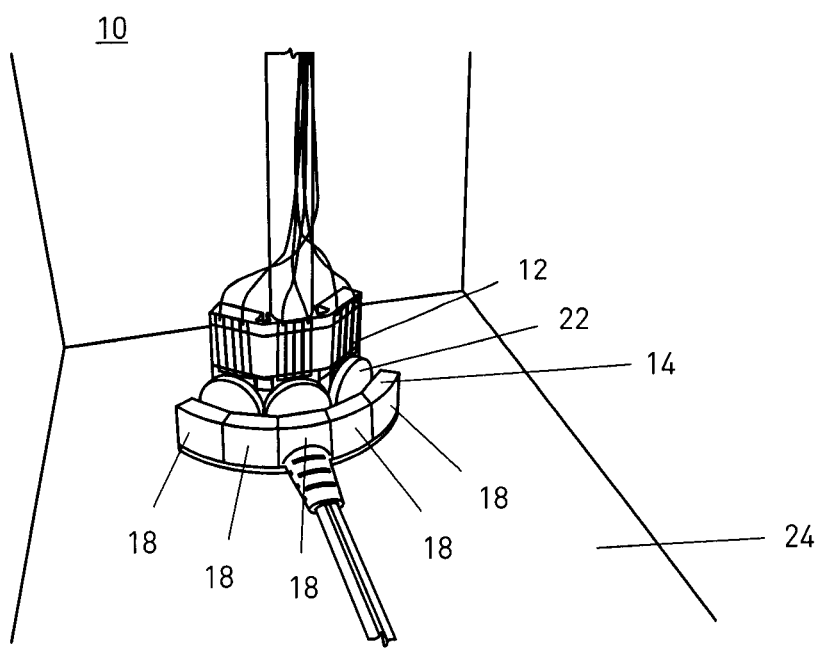
FIG. 2B is a front perspective view depicting the embodiment of FIG. 2A, the apparatus positioned in a measuring position.

Referring to FIGS. 2A and 2B, in some embodiments of apparatus 10, small size individual thermoacoustic sensors 12 can be used for measuring ultrasound power from a mouthpiece 14 of a dental device such as those described in PCT publication WO 2011/134071, incorporated by reference herein in its entirety. As described in WO 2011/134071, transducers in a mouthpiece can emit ultrasound towards the interior/cavity of the mouthpiece such that when the mouthpiece is placed over the teeth and gums of a patient, the transducers can emit ultrasound towards the patient's dental tissue. Multiple thermoacoustic sensors can be assembled into an array 16 (a three sensor array embodiment is shown in FIGS. 2A and 2B, although it would be understood that a number of sensors can be included in the array). The array system 16, for example three-sensor array, can be used to measure power from a non-planar (three-dimensional) array of transducers such as ultrasonic dental mouthpieces 14. In addition, the output ultrasound power from each individual transducer 18 from within the transducer arrays can be measured.

In order to measure the output power from mouthpiece 14, array 16 can be lowered (as shown in FIG. 2B) inside the mouthpiece cavity 20 so that the emitted ultrasound from transducers 18 inside mouthpiece 14 can be captured/incident on absorbers 22 of the sensors 12.

Measurements can be taken within a water-bath, for example, in degassed water. In some embodiments, the water in water-bath 24 can be agitated and circulated by a water pump (not shown), for example a fish tank water pump. The water can be circulated in order to maintain a constant temperature of the water across the whole volume of water-bath 24. It is known that water evaporation can cause the surface of the water to be few degrees lower than the water temperate lower in the tank, therefore water circulation can ameliorate the effects of water temperate gradients due to evaporation or due to local heating of water, for example, proximate to sensor absorber 22. The use of a water pump for water circulation can improve the repeatability and accuracy of measurements.

Use of apparatus 10 to measure and calibrate mouthpiece 14 transducers 18 can aid in providing consistent unit-to-unit ultrasonic output which can result in enhanced treatment performance and compliance with ultrasonic therapy standards of the ultrasound dental product.

Figure 3A:
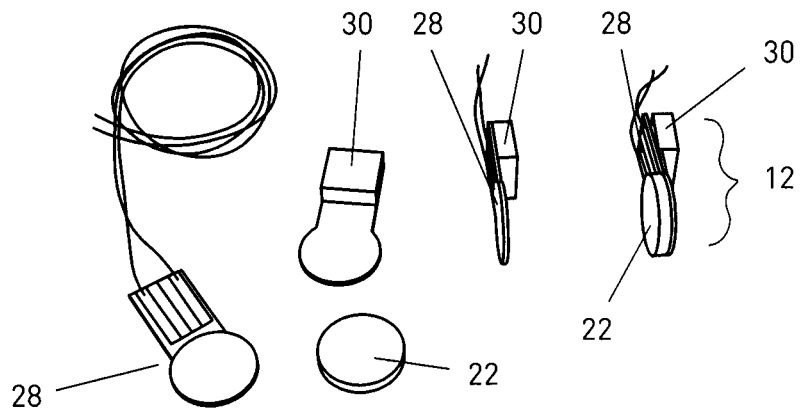
FIG. 3A is an exploded view and a side perspective view depicting an embodiment of thermoacoustic sensor.

Referring now to FIG. 3A, three components of an embodiment of ultrasound sensor 12 are depicted. In some embodiments, the components can include heat flux sensor 28, absorber disk 22, and heat sink 30. In some embodiments, heat flux sensor 28 can be a solid heat flux sensor. In some embodiments, absorber 22 can be a highly ultrasound absorbent material. In some embodiments, absorber 22 can be rubber. In some embodiments, absorber 22 can be butyl rubber, ethylene propylene rubber, polyurethane rubber, or silicone rubber. In some embodiments, heat sink 30 can be copper.

In some embodiments, thermoacoustic sensor 12 can comprise heat flux sensor 28, an absorbing layer 22 attached to one side of heat flux sensor 28 and an optional heat sink 30 attached to the other side of heat flux sensor 28. FIG. 3A depicts heat flux sensor 28 attached, for example soldered, to heatsink 30, and also, an assembled ultrasound sensor 12 with the absorber attached, for example glued, to the heat-flux sensor 28.

In some embodiments, the absorbing layer 22 can be formed onto the heat flux sensor 28 by pouring (potting) an elastomer (liquid rubber) on the heat flux sensor 28 surface and subsequent polymerization (curing) of the elastomer for it to harden. This approach can ensure good attachment of the absorbing layer 22 to the heat flux sensor 28 surface and minimize or eliminate any air gap between the two.

In some embodiments, methods of attaching a solid heat flux temperature sensor 28 to heat sink 30 can include using a thermal paste. In some embodiments, solder or conductive epoxy can be used to attach the components. Using epoxy, the attachment can be strong but irreversible once the epoxy cures. Using solder paste, the attachment can be strong, and if the solder is reheated, the heatflux sensor can be removed from the heat sink (if required for servicing, etc). An example of such a solder paste is a low-temperature lead-free solder (140 C melting point) 57Bi/42Sn/1Ag.

In some embodiments, methods of attaching the ultrasound absorbing layer 22 (in this example butyl rubber or silicone rubber) to one side of the heat flux temperature sensor 28 can include attaching the two parts using common thermal paste, but the heat conductivity at the interface of the two materials can change if the rubber layer moves relative to the heat flux temperature sensor, which can negatively affect the calibration of the sensor. In some embodiments, a thin layer of rubber or silicone adhesive can be used, or attachment can be accomplished be "fusing" the rubber to the surface of the heat flux temperature sensor. "Fusing" can be accomplished by heating up both the rubber and the heatflux temperature sensor, and attaching the rubber the heat flux sensor while applying mechanical pressure on the rubber to ensure no air is trapped at the interface of the two materials.

Figure 3B:
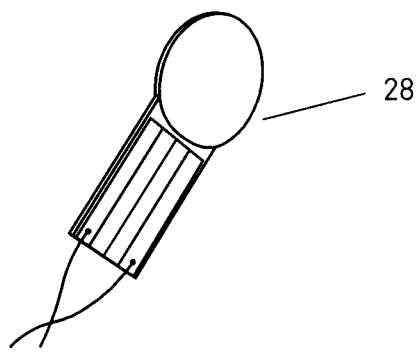
FIG. 3B is a front perspective view depicting an embodiment of a heat flux sensor.
Figure 3C:
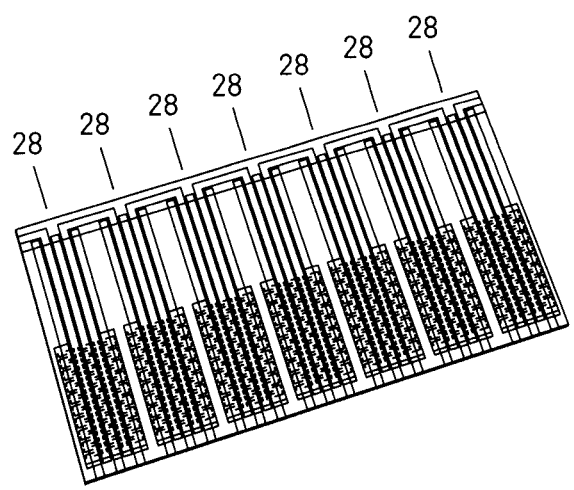
FIG. 3C is a front perspective view depicting an embodiment of an array of heat flux sensors.

FIG. 3B, depicts a solid heatflux sensor 28 type, where the two facets of the sensor are solid and made of copper. FIG. 3C, depicts an array of flexible heatflux sensors 28 which can be utilized in further embodiments of ultrasound measuring apparatus 10 and methods. The two facets of a flexible heat flux sensor array can be made of a flexible insulating material.

In some embodiments, thermoacoustic sensor 12 can be used for measuring acoustic power of the ultrasound transducers in the range of 1-100 MHz.

Certain advantages of the present design based on a heat flux sensor 28 can become apparent. The use of heat-flux sensor 28 can give very precise and stable data about the temperature difference between the two sides of the heat flux sensor 28 (for example, between the front absorber 22 and water in water bath 24 or heatsink 30 on the back). In some embodiments, the temperature difference between the two sides of the heat flux sensor can be a spatial average (across the heat flux sensor facet) temperature difference. Heat flux sensors do not respond to absolute temperature, but generate an output voltage proportional to the spatial average temperature difference between the front and back of the heat flux sensor. In addition, the use of a heat-flux sensor 28 does not necessarily require a reference temperature reading and other complex electronics, and can allow for temperature/ultrasound readings when the ultrasound power is constantly on but is slowly increasing or decreasing.

The ability to measure slow drifting ultrasound power has important implications as it can allow for tuning/adjusting a transducer emitting ultrasound power level while measuring the output power in real time (no need to turn off the ultrasound transducer, adjust the electronics driving the transducer, and then measure the emitted power again). Therefore, the present apparatuses and methods can allow for the use of a real-time closed loop for calibration of the transducer emitted power based on a digital or analogue output signal of ultrasound sensor 12 that can feed into the calibration input port of the electronics driving a transducer. As such, an automated and fast calibration process is provided. The same can also allow for the observation and measurement of any slow drift in the ultrasound power level of the transducer.

In some embodiments, a new method of calibrating a thermoacoustic sensor or integrating sphere is provided wherein only the maximum power measured by a balance power meter is used.

In some embodiments of the apparatuses and methods described herein, heat flux can be generated by incident ultrasound waves being absorbed in the absorbing layer 22 and transformed into heat. Heat flux sensor 28 can measure the heat flux from the absorbing layer 22 while the back of the heat flux sensor can be maintained at constant temperature by heat sink 30 (the heat sink 30 can be absent in which case the water bath 24 surrounding thermoacoustic sensor 12 can play the role of heat sink). The heat flux temperature sensor 28 can give the total ultrasound power absorbed by the entire surface of the absorber 22 of the thermoacoustic sensor 12, not just at some local point (as in the case of a thermistor or a thermocouple temperature sensor). A heat flux sensor 28 can integrate the ultrasound power over its surface, and it does not require additional components such as metal layers for uniform temperature distribution, thereby avoiding/ameliorating the variability problem induced by adding additional layers.

Other heat measuring methods can have further disadvantages. Using thermocouple or thermistors can give local measurements instead of a comprehensive measurement of the heat. In addition, extra local heat can be generated at the wire/rubber interface causing viscous heat artefact.

Castor oil calorimeters rely on castor oil which has a relatively low absorption coefficient, for example at 1.5 MHz $\alpha=0.12$ mm$-1$ (0.52 dB/mm). Rubber materials may have absorption coefficient >4 dB/mm at 1.5 MHz, which is much larger than that of castor oil, and so can achieve the same absorption with much thinner absorption layer.

In some embodiments, apparatus 10 can be used to observe and measure variations of the ultrasound power from transducer 18 to transducer 18 in the same ultrasound device or from one device to another, for example the same mouthpiece 14 and from mouthpiece 14 to another mouthpiece 14. The reproducibility and repeatability of power measurements can be significantly improved as the large and varying measurement error caused by positioning an ultrasound device in the prior art balance can be eliminated. Apparatus 10 can be used to measure the near field ultrasound, while with the prior art balance power meter, there is uncertainty as to if near field or far field ultrasound waves were being measured. This prior art problem is particularly the case when small size transducers are used as they have a shorter near field ultrasound range. In addition, apparatus 10 or heat flux sensor 12 can be used to observe subtle ultrasound power variation over long periods of time that can be caused by shifts from electronics (possibly due to heating of the electronics, etc.), and provide further insight into functionality and stability of the electronics driving the transducers.

In some embodiments, the heat flux sensor can be a quasi-DC voltage source (when one side of the sensor is heated up such as the case when the ultrasound absorbing layer 22 absorbs ultrasound) without high frequency components. As such, multiple heat flux sensors can be used (such as in an array or arrays) without worrying about electrical cross talk.

Figure 4A:
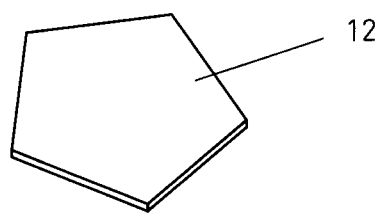
FIG. 4A is a front perspective view depicting an embodiment of thermoacoustic sensor.

In addition, some embodiments of an ultrasound power sensor 12 based on a heatflux temperature sensor 28, can be easily scaled (for example, from 5 mm to 300 mm), can have various shapes (for example, round, square, pentagon (as depicted in FIG. 4A), or any other appropriate shape), can be insensitive to the angle of incidence of the ultrasound beam, can be insensitive to the beam shape, can be insensitive to vibrations, can be small size (slim shape), can be arranged in arrays, can measure inside a cavity (such as a mouthpiece 14), can be fast and easy to position, and not require transducer manipulation (stretching, pushing, etc).

In some embodiments, the ultrasound sensor 12 can be larger than the emitting transducer 18 and one sensor 12 can capture the entire ultrasound beam of an emitting transducer 18. For example, this is the case for the apparatus 10 used to measure the ultrasound from transducers in mouthpiece 14 where round solid heatflux sensors 28 can be used.

In some embodiments, apparatus 10 and/or an acoustic integrating sphere, as described herein, can further comprising means for reporting a temperature difference detected by the sensor, the means for reporting a temperature difference being in electronic communication with the sensor. The means for reporting a temperature difference can comprise software configured for converting the temperature difference to data. In addition, the software can be further configured for converting the data to a measurement of ultrasound. The means for reporting a temperature difference can also include a display device for the software to display the temperature difference, the measurement of ultrasound power, and/or the ultrasound profile of the emitted ultrasound.

In some embodiments where a flexible array of multiple heatflux sensors 28 are used, more than one sensor can be required to capture the beam from a single emitting transducer. In these situations, multiple sensors 12 can measure a portion of the total emitted ultrasound power, and a software application can display and add the values from the multiple sensors 12 to give the total power emitted by the transducer 18. In some embodiment, the software and a graphical user interface can provide a link between the sensor's hardware and a general purpose or specific purpose computer.

Figure 4B:
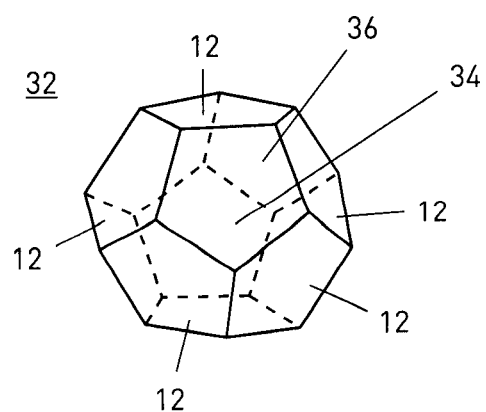
FIG. 4B is a schematic diagram of a perspective view depicting an embodiment of an acoustic integrating sphere.

In some embodiments, an acoustic integrating sphere for total acoustic power measurements is provided. Referring now to FIG. 4B, multiple thermoacoustic sensors 12 (as described herein or otherwise) can be configured in a certain manner to form the approximate shape of a sphere 32.

The term 'sphere' as used herein is used for convenience and is a term of approximation and not precision. It is used as a term of description and not of limitation, and there is no intention in the use of such term of excluding equivalents of the features shown and described or portions thereof. A 'sphere' as used herein can include any number of three dimensional geometric shapes forming a cavity or a space between two or more walls in which ultrasound can be emitted into. In some embodiments, the area of opening leading to the cavity is proportioned to be much smaller than the total area of the cavity.

Similar scenarios as described herein can apply to an integrating sphere 32, where an ultrasound beam from a transducer head may fall on multiple thermoacoustic sensors 12 of the sphere 32 interior 34, and sphere control software can then provide the total power (the sum) captured by all exposed thermoacoustic sensors 12. In addition, a software system can provide the ultrasound power incident on each sensor 12, therefore providing a spatial map of the ultrasound beam profile (providing the angular distribution of emitted ultrasound power). The smaller the size of each sensor 12, the better spatial resolution of a beam profile can be obtained. Such an approach can replace the need of complex hydrophone measurements and alignment system to determine the beam profile/shape.

In some embodiments, the apparatuses and methods as described herein can be used for measuring total acoustic power of ultrasound transducers and can include the feature of not being sensitive to the beam shape or direction of the emitted ultrasound wave, therefore not requiring alignment of the ultrasound transducer head relative to the integrating sphere position (other than ensuring the transducer head emitted ultrasound enters the sphere at any angle). This is not the case for the prior art radiative force balance type ultrasound power meters that are intended to be used with the ultrasound transducers emitting an ultrasound beam with parallel beam/plane wave, or the scanning technique using a hydrophone that requires alignment of the hydrophone sensing element (such as made of polyvinylidene fluoride (PVDF) film) perpendicular to the ultrasound beam direction/parallel with the ultrasound wave front. The apparatuses and methods as described herein can also be used for measuring the total acoustic power emitted by ultrasound heads comprising multiple ultrasound transducers including ones forming a non-flat array, for example non-collinear transducers.

To measure the power emitted from the head of an ultrasound device, the head can be inserted or placed proximate to an opening 36 into sphere 32. Sphere 32 can be filled with water, or other suitable fluid, and the transducer head can be immersed in the water in order to couple the ultrasound waves to the water and then to the sensing surface of the sphere interior 34 walls. The voltage generated by sphere 32 can be proportional to the absorbed (emitted) ultrasound power. The whole sphere could also be immersed in a water bath. The liquid inside the sphere 32 and the liquid outside the sphere 32 could be circulated using a water pump, for better accuracy and repeatability of the measurements.

An integrating sphere 32 for measuring/characterizing ultrasound power can comprise a cavity 34 assembled from individual thermoacoustic sensor 12 elements filled with a liquid that is kept at constant temperature. In some embodiments, each thermoacoustic sensor 12 can have the shape of a pentagon (as shown in FIG. 4A), with the sensitive surface facing the interior 34 of sphere 32. Assembling eleven such sensors 12 (one pentagon facet can be removed to form an opening 36 in sphere 32) a dodecahedron can be formed, which acceptably approximates a sphere (as shown in FIG. 4B). Choosing to use more elements can result in a shape closer to an ideal sphere.

In addition, a sphere with more than one opening can be used as needed for each specific application. Furthermore, multiple sensors 12 (round shaped or with other shapes) can form arrays with various shapes such as cylinders, cubes, cube corners, cones, etc, as needed for specific applications.

Individual thermoacoustic sensors 12 can comprise at least two parts: an ultrasound absorbing material 22 with an acoustic impedance matching the acoustic impedance of the liquid inside the cavity and a temperature sensor, for example, but not limited to a heat flux sensor 28. Multiple embodiments of the thermoacoustic sensor 12 can be used for an integrating sphere design.

In some embodiments, a sensor 12 can be used incorporating a thermistor or thermopile sensor (instead of a heat flux sensor) that can generate an electrical output (voltage or change in the resistivity) proportional to the temperature of the back surface of an absorbing material.

Figure 5A:
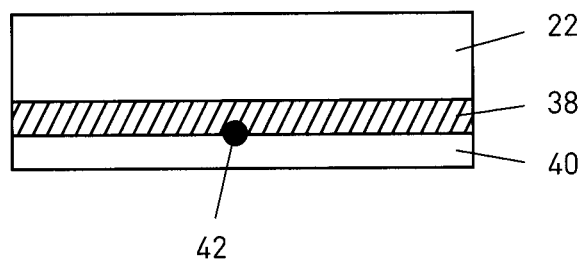
FIG. 5A is a schematic diagram of a cross-section view depicting an embodiment of a thermoacoustic sensor.

Referring now to FIG. 5A a sensor can comprise a layer of material 22 that can have both a high ultrasound absorption coefficient and an acoustic impedance Z close to that of water Z=1.5 MRayl, a layer of material with high thermal conductivity 38 (for example, silver, copper aluminum, pyrolitic carbon), a layer of thermo-isolating material 40 (for example, a closed cell foam) or structure (like air or vacuum flask), and a thermistor/thermopile 42 or other temperature sensor that senses the temperature of the conductive layer 38.

Figure 5B:
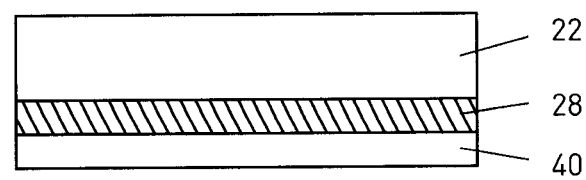
FIG. 5B is a schematic diagram of a cross-section view depicting an embodiment of a thermoacoustic sensor.

In some embodiments, and referring now to FIG. 5B, a sensor 12 can be used incorporating a heat flux sensor 28 that generate a voltage output proportional to the heat flux from the back surface of an absorbing material 22. Sensor 12 can comprise a layer of material 22 with both a high ultrasound absorption coefficient and an acoustic impedance Z close to that of water Z=1.5 MRayl, a heat flux sensor 28, and an optional external heat sink 30 kept at constant temperature.

The use of an ultrasound absorbing material 22 that also has an acoustic impedance close the surrounding water can make the thermoacoustic sensor 12 insensitive to the angle at which the ultrasound wave impinges the absorber. This is because the ultrasound wave will see no boundary (from an ultrasound wave propagation perspective) at the water/absorber interface. This results in the ultrasound wave being absorbed in the absorber material 22 independent of the incidence angle. In addition, because the absorber 22 can closely match the acoustic impendence of water, there is no (or little) reflection of ultrasound at the water/absorber interface, therefore avoiding or reducing ultrasound wave ring cavity propagation (bouncing from a sensor to another until fully absorbed) inside the sphere.

Referring now to FIGS. 6A-6D, in some embodiments, the acoustic integrating sphere can be configured to be a data acquisition/measuring unit. Cavity 34 can be designed, configured, and built in such a way that it has almost 4pi ($4\pi$) solid angle acceptance angle of ultrasound waves. Sphere 32 can have a small opening 36 for the insertion of an ultrasound head 44 from an ultrasound device. An example of a cavity 34 made in the shape of a dodecahedron is shown. The cavity 34 can be filled with water or other suitable measuring liquid. For improved accuracy the liquid (as well as the external heat sink 30 if used) can be thermo stabilized with a help of a heat exchange and/or water circulation.

Certain advantages of an acoustic integrating sphere 32 as described herein can become apparent.

As the internal liquid (water or other coupling medium) inside sphere 32 can be kept at constant temperature, the measuring instrument 10 can be immune to the heat generated or introduced by the ultrasound head (emitter).

The total power of the ultrasound emitted can be measured independent of the shape of the ultrasound emitting elements or the beam profiles (divergent, parallel, and convergent) and beam shapes (circular, elliptical, etc). See FIGS. 6A and 6B for examples of different device shapes and beam profiles.

The present apparatuses and methods can have an ability to measure much faster and be more sensitive than a traditional prior art calorimeter (filled with a castor oil for example) as the absorbing element 22 can have much smaller mass. In the castor oil calorimeter the absorbed ultrasound heats up the whole volume of the oil in the calorimeter, in the apparatuses and methods described herein, the ultrasound only heats up the ultrasound absorbing layer 22 of sensors 12.

Acoustic integrating sphere 32 can have an interior 34 surface sensitive to ultrasound and can be used to measure the total power from any ultrasound transducer (imaging, therapeutic or interventional) with any beam shape and profile (convergent, divergent, parallel, circular, oval, etc) through an aperture/opening 36 in the sphere. Acoustic integrating sphere 32 can also provide the ultrasound beam spatial profile (angular distribution of emitted ultrasound power) with a spatial resolution dependent on the size/area of each sensor 12 of the sphere 32.

Acoustic integrating sphere 32 can also address the portability issues of prior art systems, and can bring the measurement/calibration system to the ultrasound system location.

In addition, sphere 32 can have one or more sensors that can read the frequency of the incoming ultrasound waves. For example these can be small PVDF sensors located in the interior 34 of the sphere. As the ultrasound absorbing layer 22 can have a frequency dependent ultrasound absorption, the reading of the ultrasound wave's frequency can then be used in the calibration constant for a more precise instrument measurement over a wide ultrasound frequency range. Practically the heat is deposited in the absorber 22 at different depths (deeper for lower frequency, closer to the surface for higher frequency) and a heat flux temperature sensor 28 can see a different effective heat for ultrasound with different frequencies. Some embodiments of the apparatuses and methods described herein can allow for the individual sensor 12 and the integrating sphere 32 to operate over a wide range of frequencies with high precision.

Figure 7:
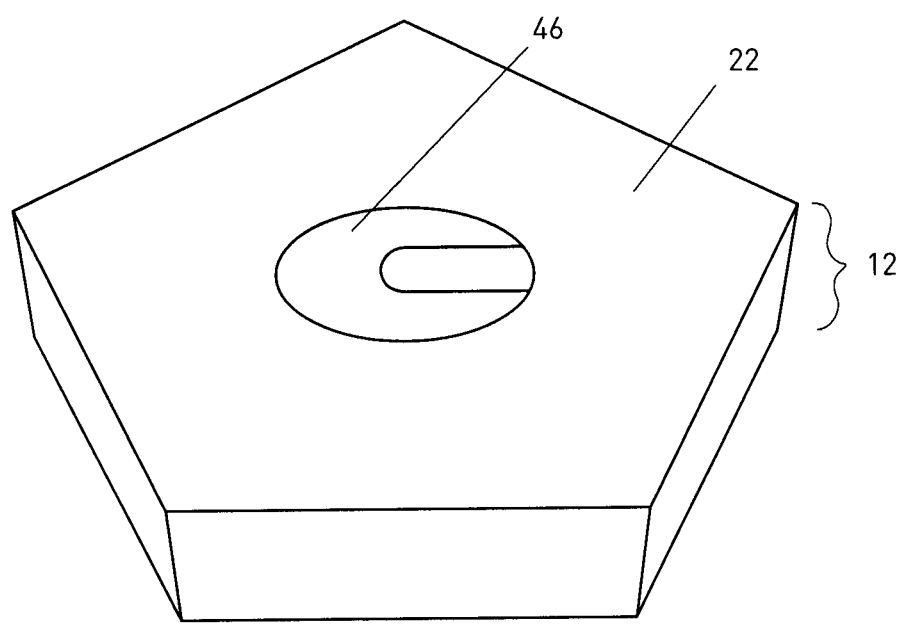
FIG. 7 depict an embodiment of an ultrasound sensor that integrates a membrane hydrophone and an ultrasound thermoacoustic sensor.

In addition, and as depicted in FIG. 7, each individual sensor 12 of sphere 32 can be equipped with an optional piezoelectric sensor (or other sensor) sensitive to acoustic pressure. One possible implementation can be a thin PVDF membrane hydrophone 46 (such as the one depicted in FIG. 1D) attached (glued, deposited, or otherwise appropriately attached) on top of absorber layer 22 of a thermoacoustic sensor 12. Another implementation can be a membrane hydrophone incorporated within the rubber or between two layers of rubber. The integration of a membrane hydrophone can allow the sensor 12 or sphere 32 to also be able to measure the frequency and bandwidth of the ultrasound wave. Another implementation can be a resistive heater incorporated inside the rubber or between two layers of rubber. The heater can be powered from an external electrical circuit in order to heat up the rubber as it would happen when ultrasound is absorbed by the rubber. As a result, this heater can be used for self-calibration of the thermoacoustic sensor without the need of an external reference ultrasound emitting transducer. As the PVDF film of the membrane hydrophone and the resistive heater can be only several micrometers thick, the presence of the PVDF film or resistive heater will not affect the ultrasound propagation through the absorber or reflection from the absorber.

Absorber 22 material can be a highly ultrasound absorbing material (with a high absorption coefficient with acoustic impedance Z very close to the media used for coupling the ultrasound wave (usually water or gel with acoustic impedance 1.5 MRayls). Such absorber 22 material can be different types of rubber such as: butyl rubber, butyl rubber fusion tape, ethylene propylene rubber fusion tape, or silicone rubber doped with different powders (W, Ni, $SiO_2$, $Fe_2O_3$, $Bi_2O_3$, etc.) or with resins and/or epoxies. As these rubbers can be fabricated to have similar acoustic impedance with water, there is no (or little) reflection at the rubber/water interface, which can make measurements independent of the ultrasound beam incident angle. For this reason these rubbers, in particular butyl rubber and/or doped silicone rubber, are preferred materials for ultrasound absorption layer 22.

Butyl rubber can be highly absorbent of ultrasound and, for example, using an approximately 3 mm thick rubber can limit back reflection from the rubber to heat flux sensor interface. Silicone rubber can also be a strong absorbent of ultrasound and, using an approximately 1 mm thick rubber can limit or eliminate back reflection from the rubber to heat flux sensor interface. In these examples, the thickness of the butyl rubber or silicone rubber can vary depending on the ultrasound absorption coefficient of the specific material production batch.

The absorption is frequency dependent in rubbers, therefore for higher frequencies a thinner layer of rubber can be used if needed, which can shorten the response time of the thermoacoustic sensor, making the measurement times shorter.

In some embodiments the ultrasound absorbing layer can have more than one layer of rubber with different acoustic and thermal properties.

Without any limitation to the foregoing, the present apparatus and method is further described by way of the following examples.

EXAMPLE 1

Introduction

A use of a multi-sensor ultrasound power meter is to provide simultaneous measurement of the ultrasound power from several transducers in an ultrasound transducer array, for example, in a mouthpiece. Some embodiments can allow for measurement of up to three buccal transducers in either maxilla or mandible mouthpieces.

In comparison with a different embodiment of a thermoacoustic power meter a circulation of the water in the measurement tank can be implemented. By providing the water circulation in the tank it becomes possible to significantly improve repeatability and reproducibility of the system.

Operation of the device is based on the thermal effects of ultrasound waves. When an ultrasound wave is absorbed in absorbing medium it generates heat. This causes the temperature of the medium to rise. The temperature continues to rise until the rate of heat losses (which are, for most cases, proportional to temperature difference between the absorbing media and the surrounding heat sink) becomes equal to rate of the heat generation. In the simplest case when the absorbing body has a shape of a thin parallelepiped, the heat is lost mainly through the two largest facets of the parallelepiped. Thus, by measuring the heat losses (heat flux) through one of these surfaces, one can evaluate the absorbed ultrasound power. The detailed principle of the thermoacoustic ultrasound power measurement can be found in references 1 to 5.

One of the most accurate ways to measure the heat flux through a surface is to use a heat flux sensor. A heat flux sensor is essentially a very thin thermopile with very small temperature resistance. It generates voltage output proportional to the value of the heat flux through the sensor.

The ultrasound absorbing target material should have high ultrasound absorption coefficient and an acoustic impedance close to the surrounding material (usually water or gel with R=1.48 MRayl). In the 1.5 MHz frequency range, butyl rubber and silicone rubber have some of the most ideal properties relating to intensity absorption coefficient and acoustic impedance.

EXAMPLE 2

Setup

The setup for measuring acoustic power can consist of two units: a thermoacoustic multi-sensor head and a data acquisition module with appropriate software.

The Multi-sensor Thermoacoustic Head

Figure 8A:
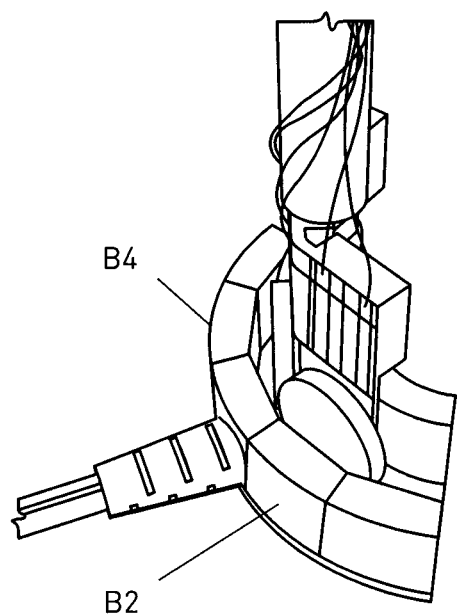
FIGS. 8A and 8B depicts and embodiment of a multi-sensor head in the position for measuring power from transducers (8A—B2 and B4, 8B—B1, B3, and B5 of a dental ultrasound mouthpiece).
Figure 8B:
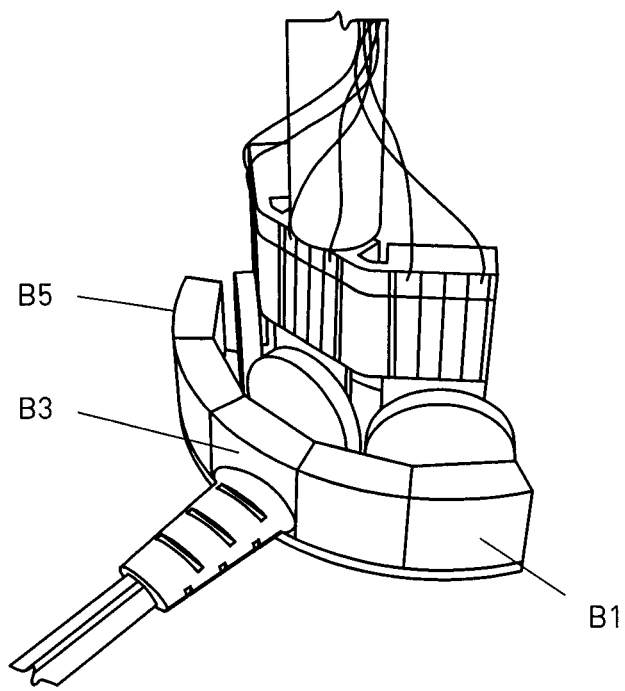

The multi-sensor thermoacoustic head can include three individual thermoacoustic sensors mounted on a common heat sink. Each sensor is a round (20 mm diameter) mm heat flux sensor (Captec™ Inc.) covered with two 1.5 mm layers of butyl rubber. The layout of the sensor is shown in the FIGS. 8A and 8B.

Figure 9:
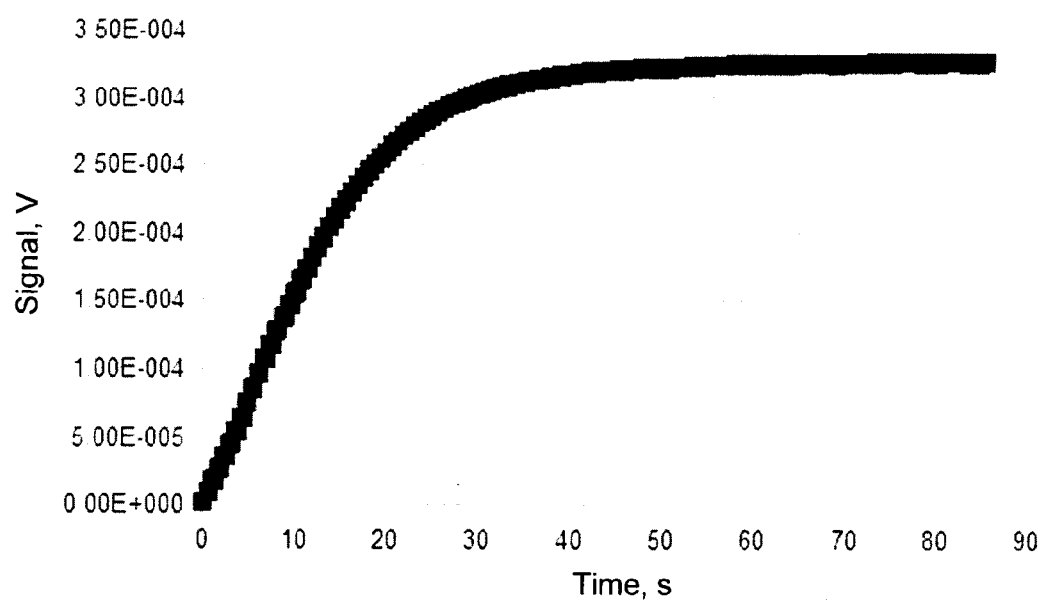
FIG. 9 depicts typical time dependence of the output voltage of a thermoacoustic sensor in response to being exposed to acoustic power. (Sensor output voltage [Volts] vs time [seconds]).

In steady state conditions the sensor generates constant voltage proportional to the power of the ultrasound wave. When the sensor is irradiated by the step function ultrasound wave, it generates an output voltage that has a distinct saturation-like shape. The typical diagram is shown in FIG. 9.

In the case of the step like power function (turn ON) it is possible to obtain the correct value of the ultrasound power even before the output voltage of the sensor has reached the steady state by knowing the law that the voltage waveform follows. Essentially in this case the ultrasound power is proportional to the asymptotic value of the output voltage. This asymptotic value can be obtained with a help of regression analysis (fitting). After a calibration procedure establishes the relation between the parameters of the model and the power of the ultrasound wave, one can uniquely calculate the ultrasound power from the experimental data. It was found that the following function gives a very good fit for the time dependence of the output signal from the sensor:

$$S(t)=C_0+C_1(1-e^{(-t/C_2)}),$$

where "e" is Euler's number and where fitting parameters $C_0$, $C_1$, $C_2$ have the following meaning: $C_0+C_1$ is a horizontal asymptote that is proportional to the power of the ultrasound wave, $C_2$ is a time constant and t is the time.

It has been found that the signal from the thermoacoustic sensor is influenced to some extent by the cooling conditions. To minimize such influence and to provide also the faster return of the sensor output to zero after the removal of the ultrasound power the water in the measuring tank is kept under intense circulation.

EXAMPLE 3

Validation of Device Operation

The following performance characteristics of the multi-sensor thermoacoustic power meter have been validated: parasitic crosstalk between the individual sensors in the array, non sensitivity to the power emitted from back side of the sensor, sensitivity to the lower power level ultrasound (10-50 mW).

Figure 10:
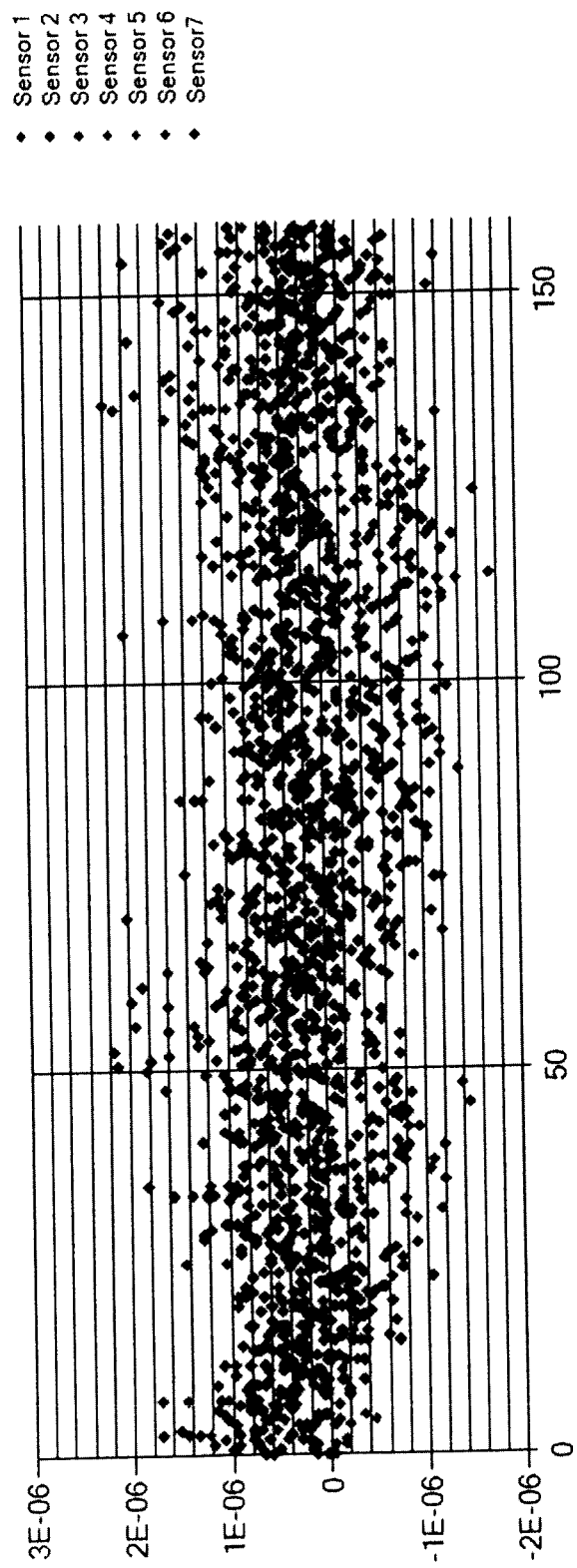
FIG. 10 depicts output signal of a multisensory head (sensors 1, 2 and 3 are active) when the sensors face a buccal side of an ultrasound mouthpiece and the lingual transducers are ON. 1×10-6 digits correspond to approximately 0.5 mW of ultrasound power. (Sensor output voltage [Volts] vs time [seconds]).

Non sensitivity to the ultrasound power emitted from the back of the sensor: To determine sensitivity of the sensor to the ultrasound power emitted from the back direction, the sensor was placed inside the mouthpiece so that the sensors face the buccal transducers. The power of the buccal transducers was set to zero and the power of the lingual transducers was set to maximum. The output of the multi-sensor head is shown in the FIG. 10. As one can see from FIG. 10, the signal from the sensors does not exceed the noise level.

Figure 11:
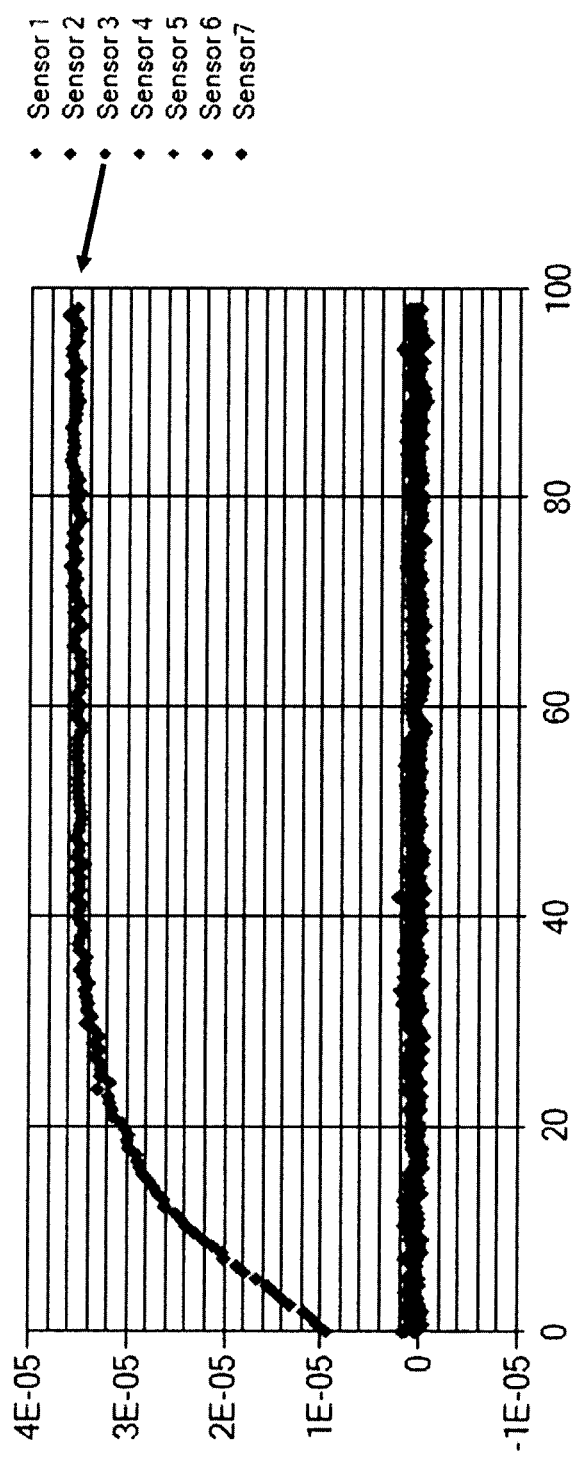
FIG. 11 depicts an example the output of a 3-sensor power meter in the case when only transducer B5 is active. Sensor #1 faces B1, sensors #2 faces B3, sensor #3 faces B5. (Sensor output voltage [Volts] vs time [seconds]).

Confirmation of the absence of the crosstalk: Experiments were performed to verify that each of the sensor in the multi-sensor head is sensitive to the ultrasound power emitted from its "area of responsibility" and not sensitive to the ultrasound power emitted outside of this area. For example, in the standard position for mandible mouthpiece as in FIG. 8B, sensor #1 should measure power emitted from the transducer B1, but should not be sensitive to the power emitted from transducers B3, B4, B5; sensor #2 measure power from B3, but not from B1 and B5; sensor #3 from B5 but not from B1, B2, B3. The result of the experiments confirmed that there is no parasitic cross talk between the sensors (See FIG. 11 as an example where transducer B5 is active).

EXAMPLE 4

Reproducibility and Repeatability Verification

To investigate the reproducibility and repeatability of the system, a number of tests have been performed. The results are shown below.

TABLE 1

Output power of a mouthpiece measured at two different days with different orientation of the water pump. Three (B1, B3, B5) or two (B2, B4) transducers were emitting power simultaneously during the measurements.

| transducer | 1 | | | | 2 different water circulation conditions | | | | | average | st. dev | st. dev % |
|---|---|---|---|---|---|---|---|---|---|---|---|---|
| B1 | 19.3 | 20.2 | 19.7 | 15.1 | 20.5 | 18.6 | 20.4 | 22.4 | 21.7 | 19.8 | 2.1 | 10.6 |
| B2 | | | | | | | | 17.7 | 19.3 | 18.5 | 1.1 | 6.1 |
| B3 | 24.3 | 23.6 | 19.9 | 19.7 | 20.9 | 20.4 | 22.1 | 24.1 | 22.1 | 21.9 | 1.8 | 8.2 |
| B4 | | | | | | | | 23.3 | 22.3 | 22.8 | 0.7 | 3.1 |
| B5 | 14.6 | 15.0 | 14.6 | 14.6 | 14.3 | 14.3 | 14.7 | 16.0 | 15.0 | 14.8 | 0.5 | 3.5 |

TABLE 2

Output power of a mouthpiece measured with sensor being repositioned between the measurements. Three transducers (B1, B3, B5) were emitting power.

| | | | | | | | average | st. dev | st. dev % |
|---|---|---|---|---|---|---|---|---|---|
| B1 | 14.5 | 14 | 15 | 12.6 | 13 | 13 | 13.8 | 1.0 | 6.9 |
| B2 | | | | | | | | | |
| B3 | 17.9 | 18.4 | 21.7 | 16.7 | 18.5 | 18.3 | 18.6 | 1.7 | 8.9 |
| B4 | | | | | | | | | |
| B5 | 8 | 8.7 | 8.5 | 8.4 | 8.5 | 9.1 | 8.4 | 0.4 | 4.3 |

As one can see from the table the statistical error does not exceed 11%. One can also see that the multi-sensor power meter provides enough resolution and sensitivity to measure ultrasound power at 10 mW level with better than 10% accuracy.

Figure 12:
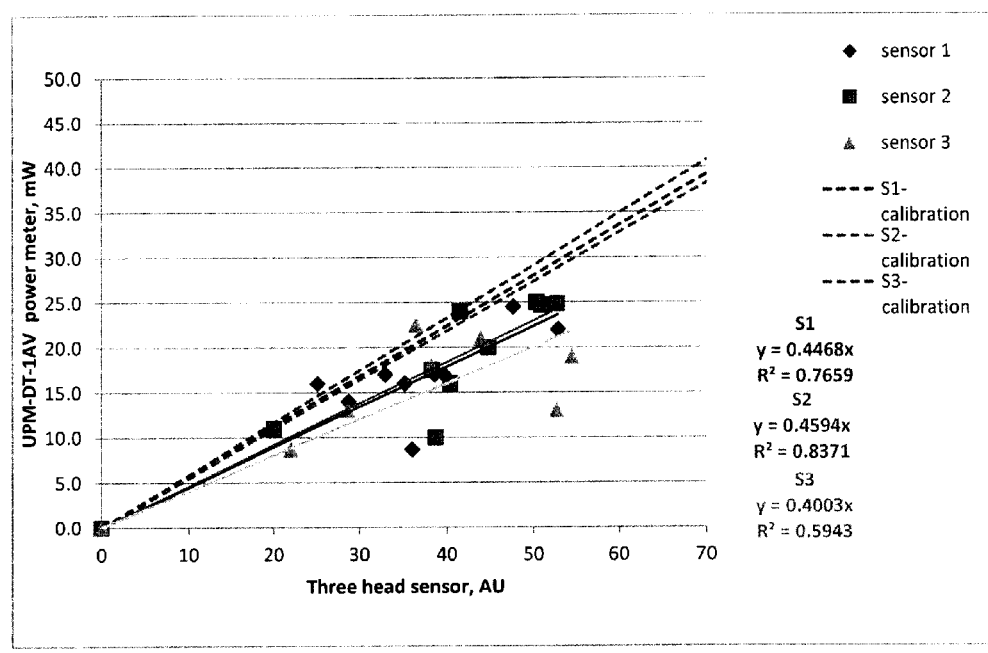
FIG. 12 depicts average values of ultrasound power emitted by different transducers measured by radiation force power meter (UPM-DT-1AV) and the multi-sensor thermoacoustic system. (UPM-DT-1AV measured ultrasound power [mW] vs ultrasound power measured by an embodiment of the thermoacoustic power meter as described herein [arbitrary units])

Comparison with radiation force power meter UPM-DT-1AV: As a part of the validation process the comparison of the power measurements of the multi-sensor system and a reference radiation force system was performed. To do this the power of the transducers of eight mouthpiece devices were measured with a help of two systems. Also the power of the reference transducer was measured (the correspondent curve for each sensor is shown as a dashed line). An example of the results are shown in the FIG. 12. As one can see from the figure the majority of the points lie under the calibration curve. This can be explained by the fact that the radiation force power meter displays lower than actual power when the transducer is misaligned.

EXAMPLE 5

Initial Calibration

It has been shown herein that within power range of interest (<1 W total power from the transducer and <0.5 W/cm2) the sensor has a linear response to the power of the ultrasound wave. Thus it is possible to calibrate the power measurement system using one point calibration. To minimize the chance of operator error and some unusual events, a three point calibration can be used.

To be able to measure power of the ultrasound wave it is necessary to establish a relation between the ultrasound power and the output voltage of the sensor (maximal or asymptotic value). The following procedure was used to find the correlation.

It is known that the power of the ultrasound wave, P, is proportional to the square of the amplitude of the ultrasound wave, which is proportional to the peak-to-peak voltage of the transducer ($V_{pk-pk}$):

$$P \sim V_{pk-pk}^2, \text{ or } P^{1/2} = AV_{pk-pk},$$

where A is some constant.

On the other hand, the voltage from the thermoacoustic power meter, S, is also proportional to $V_{pk-pk}^2$:

$$S \sim V_{pk-pk}^2, \text{ or } S^{1/2} = BV_{pk-pk},$$

where B is some other constant. To take into account the delayed response of the thermoacoustic sensor it is reasonable to use the asymptotic value of the output voltage given by the fitting model as $C_0+C_1$.

Therefore, measuring the ultrasound wave power from the same source at the same $V_{pk-pk}$ with a reference power meter and a thermoacoustic power meter will yield the calibration constant $C_{cal}$, such that:

$$P = C_{cal}S, \text{ where } C_{cal} = (A/B)^2$$

Figure 13A:
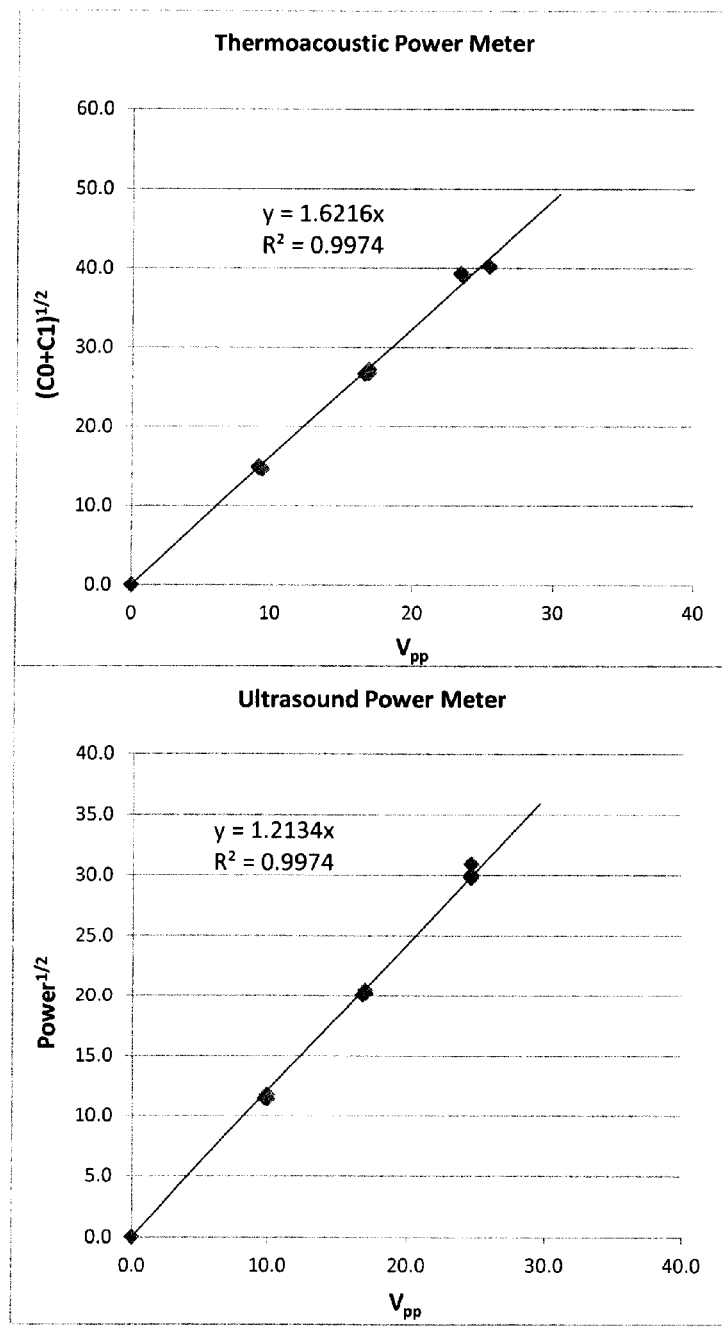
FIG. 13A depicts results of the measurements with a corresponding trend line for $P^{1/2}$ are shown for sensor 1, calibration constant for sensor #1, S1=0.56. (Top graph: arbitrary units vs $Volt_{peak-to-peak}$, bottom graph $mW^{1/2}$ vs $Volt_{peak-to-peak}$).
Figure 13B:
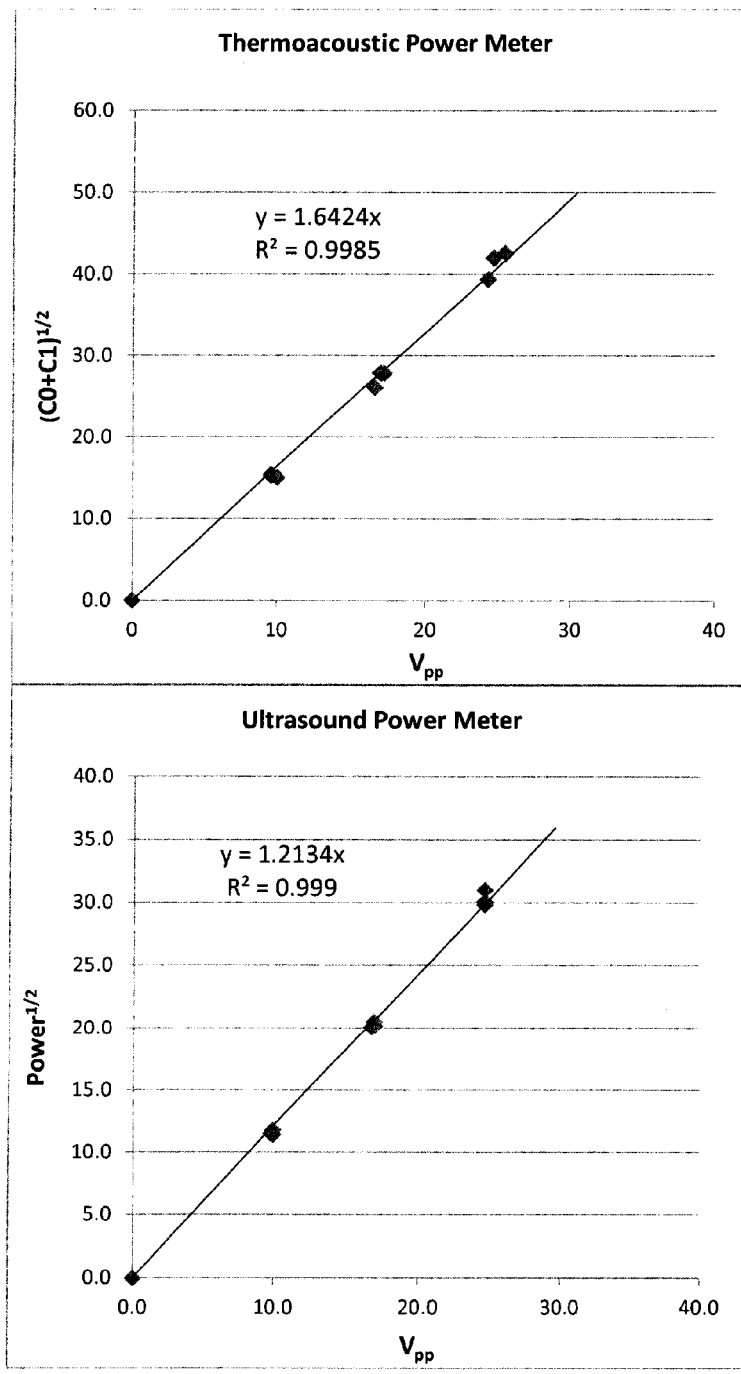
FIG. 13B depicts results of the measurements with a corresponding trend line for $P^{1/2}$ are shown for sensor 2, calibration constant for sensor #2, S2=0.546. (Top graph: arbitrary units vs $Volt_{peak-to-peak}$, bottom graph $mW^{1/2}$ vs $Volt_{peak-to-peak}$).
Figure 13C:
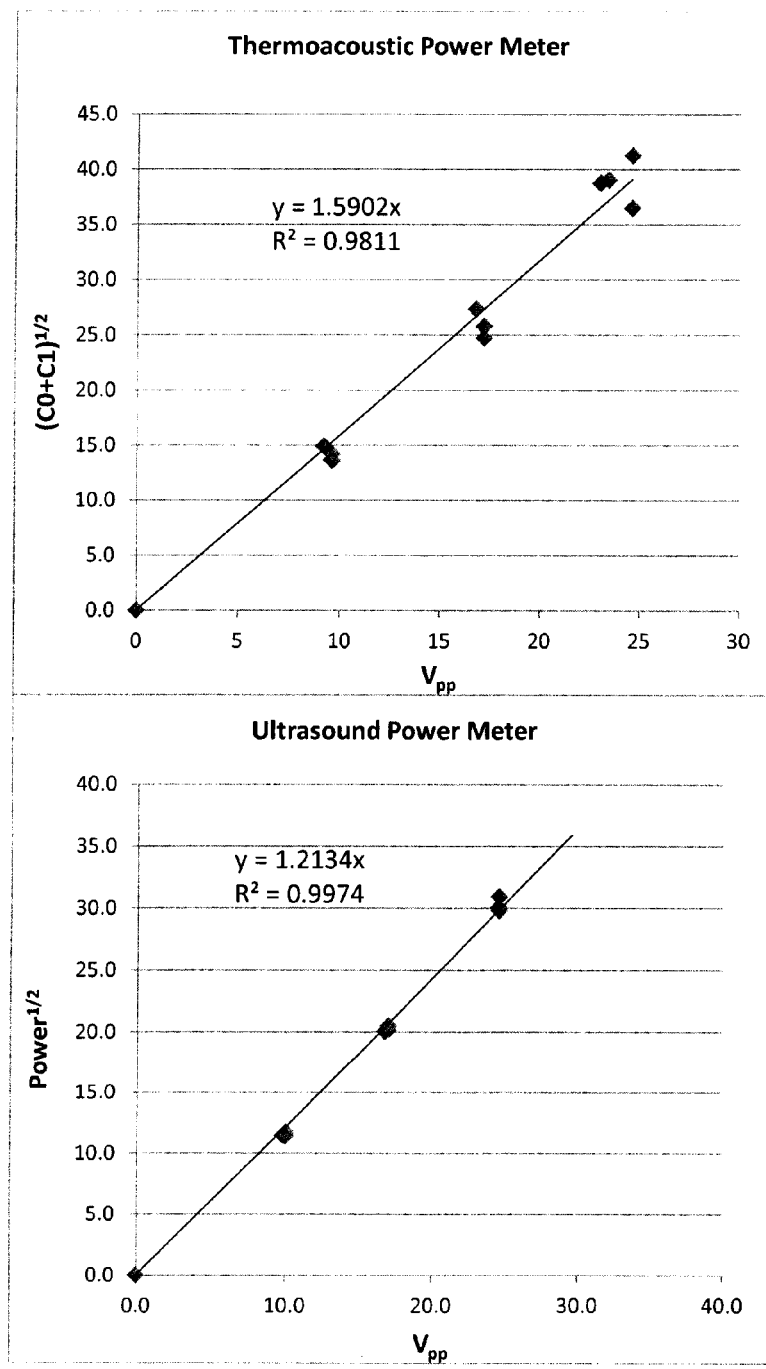
FIG. 13C depicts results of the measurements with a corresponding trend line for $P^{1/2}$ are shown for sensor 3, calibration constant for sensor #3, S3=0.582. (Top graph: arbitrary units vs Volt peak bottom graph $mW^{1/2}$ vs $Volt_{peak-to-peak}$).

To do this ultrasound power emitted by the reference transducer was measured with the help of a reference ultrasound power meter (UPM-DT-1AV). The results of the measurements with the corresponding trend line for $P^{1/2}$ are shown in FIGS. 13A, 13B, and 13C.

The scope of the claims should not be limited by the embodiments as set forth in the examples herein, but should be given the broadest interpretation consistent with the description as a whole.

Although a few embodiments have been shown and described, it will be appreciated by those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

While the above description details certain embodiments of the invention and describes certain embodiments, no matter how detailed the above appears in text, the invention can be practiced in many ways. Details of the apparatuses and methods may vary considerably in their implementation details, while still being encompassed by the invention disclosed herein. These and other changes can be made to the invention in light of the above description.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

REFERENCES

The following references are hereby incorporated into this application by reference in their entirety.
1. Zeqiri B, J Barrie, Ultrasound in Med. & Biol., Vol. 34, 1513 (2008)
2. Thermo-acoustic ultrasound sensor from GAMPT mbH http://www.gampt.de/content/cms/front_content.php?idcat=257
3. Wilken V, Measurement Sc. & Techn., Vol. 21, 115805 (2010)
4. Wilken V, Measurement Sc. & Techn., Vol. 21, 115806 (2010)
5. Martin C. J, Law A. N. R., Ultrasonics, 127 (1980)
6. Preston, R. C. (Ed.) Output Measurements for Medical Ultrasound (1991)
7. Romdhane, M., et al., Ultrasonics, Vol. 33 No. 2 (1995)
8. Fay, B, M Rinker, Ultrasonics, Vol. 34 (1996)
9. Zieniuk, J. K., Ultrasonics, 136 (1966)
10. Wells, P. N. T., et al., Ultrasonics, 106 (1963)
11. Torr, G. R., D. J. Watmough, Phys. Med. Biol., Vol. 22 No. 3 444-450 (1977)
12. Fry, W. J., R. B. Fry, J. Acoust. Soc. Am. 26, 311 (1954)
13. Romdhane, M., et al., Ultrasonics, Vol. 34 835(1996)
14. Mikhailov, I. G., Ultrasonics, 129 (1964)
15. Campolo, D. (Ed.) New Developments in Biomedical Engineering, Gutierrez, M. I., et al. Methods for Characterization of Physiotherapy Ultrasonic Transducers (2010)
16. Pullano, S. A., et al., Proceedings of the $3^{rd}$ International Conference on E-Health and Bioengineering, (2011)
17. Lubbers J., J. Schortinghuis, The weight of 1.5 MHz ultrasound. Calibration of a therapeutic unit for small animals. (2004)
18. U.S. Pat. No. 6,978,677
19. European Patent Application 83301554.8 published as 0089841
20. US 2013/0265856
21. U.S. Pat. No. 6,994,468
22. U.S. Pat. No. 8,256,953
23. US 2012/0320710
24. U.S. Pat. No. 6,490,470

We claim:

1. A thermoacoustic sensor for measuring ultrasound, the sensor comprising:
a heat flux sensor having a front and a back, for detecting a temperature difference between the front and back of the heat flux sensor; and
an ultrasound absorbing layer attached to the heat flux sensor for absorbing ultrasound and converting it to heat, the ultrasound absorbing layer also acting as an acoustic impedance matching layer.

2. The thermoacoustic sensor of claim 1 further comprising a heat sink attached to the heat flux sensor for dispersing heat.

3. The thermoacoustic sensor of claim 2 wherein the heat sink is made of copper.

4. The thermoacoustic sensor of claim 2 wherein the ultrasound absorbing layer and heat sink are on opposite sides of the heat flux sensor.

5. The thermoacoustic sensor of claim 1 wherein the ultrasound absorbing layer is made of a material selected from the group consisting of butyl rubber, ethylene propylene rubber, polyurethane rubber, and silicone rubber.

6. The thermoacoustic sensor of claim 1 wherein the heat flux sensor comprises a flexible array of heat flux sensors.

7. The thermoacoustic sensor of claim 1 further comprising means for reporting a temperature difference detected by the heat flux sensor, the means for reporting a temperature difference being in electronic communication with the heat flux sensor.

8. The thermoacoustic sensor of claim 7 wherein the means for reporting a temperature difference comprises software configured for converting the temperature difference to data.

9. The thermoacoustic sensor of claim 8 wherein the software is further configured for converting the data to a measurement of ultrasound.

10. The thermoacoustic sensor of claim 1 comprising a flexible array of heat flux sensors.

11. The thermoacoustic sensor of claim 10 wherein the flexible array is arranged in a non-flat array to match the shape of a head of an ultrasound emitting device.

12. The thermoacoustic sensor of claim 10 wherein the flexible array is arranged into a sphere like shape and facing inward to form a cavity.

13. The thermoacoustic sensor of claim 12, wherein the flexible array comprises an opening formed by the heat flux sensors to allow access to the cavity.

* * * * *